United States Patent [19]

Schohl et al.

[11] Patent Number: 4,858,460
[45] Date of Patent: Aug. 22, 1989

[54] AIR DETECTOR FOR LIQUID-FILLED SENSING LINES

[75] Inventors: Gerald A. Schohl, Knoxville; Svein Vigander, Norris, both of Tenn.

[73] Assignee: Tennessee Valley Authority, Muscle Shoals, Ala.

[21] Appl. No.: 169,917

[22] Filed: Mar. 18, 1988

[51] Int. Cl.[4] .............................................. G01N 7/00
[52] U.S. Cl. ..................................................... 73/19
[58] Field of Search ..................... 73/865.5, 865.8, 579, 73/19, 24

[56] References Cited

U.S. PATENT DOCUMENTS

| | | | |
|---|---|---|---|
| 2,573,390 | 10/1951 | Blanchard | 73/19 |
| 3,046,780 | 7/1962 | Liebermann | 73/53 |
| 3,283,502 | 11/1966 | Heisig et al. | 73/24 |
| 4,014,206 | 3/1977 | Taylor | 73/19 |
| 4,122,713 | 10/1978 | Stasz et al. | 73/19 |
| 4,122,735 | 9/1978 | McKnight | 73/19 |
| 4,130,010 | 12/1978 | Wonn | 73/19 |
| 4,144,741 | 3/1979 | Nakamoto et al. | 73/19 |
| 4,235,095 | 11/1980 | Liebermann | 73/19 |

Primary Examiner—Stewart J. Levy
Assistant Examiner—Robert R. Raevis
Attorney, Agent, or Firm—Robert A. Petrusek

[57] ABSTRACT

The present invention utilizes measurements of the characteristic standing pressure wave frequencies in normally liquid-filled pipes to detect the presence of gas bubbles or gas pockets within the pipes. Because gases, for example air, are more compressible than liquids, gas in a pipe causes the natural frequencies of standing waves to be shifted from their values with no gas. The characteristic standing wave frequencies are determined from a Fourier transform of pressure fluctuations within the pipe. The pressure fluctuations, measured using a hydrophone or other pressure transducer, are due to either background flow noise (passive technique) or a deliberately induced pressure transient (active technique). The technique is sufficiently sensitive to detect relatively small gas bubbles as well as complete gas blockage. The apparatus required depends somewhat on whether the particular application requires use of the active or passive technique. The active technique requires that a short pipe section containing a few valves and a pressure transducer be attached to the pipe that is being checked for the presence of gas. The passive technique requires only that a transducer be installed to measure pressure fluctuations. For either technique, data processing electronics are required to receive and interpret the pressure signals.

14 Claims, 10 Drawing Sheets

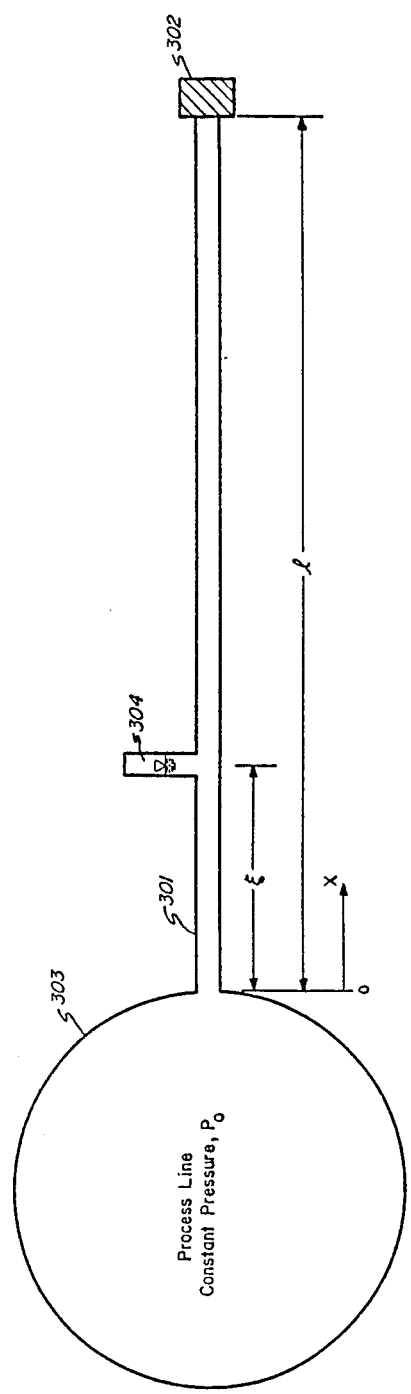

AIR DETECTOR FOR LIQUID-FILLED SENSING LINES

The invention described herein may be manufactured and used by or for the Government for governmental purposes without the payment to us of any royalty therefore.

INTRODUCTION

The present invention consists of a new, novel, and relatively simple and inexpensive, as well as highly sensitive, technique and apparatus for detecting in elongated liquid containment means the presence of bubbles or pockets of gases such as, for example, air. The methods of the present invention have been demonstrated to be eminently useful for detecting relatively small air voids, i.e., bubbles, in normally liquid-filled pressure sensing lines. The present invention relates specifically, but of course not necessarily exclusively, to the alleviation of problems heretofore associated with the detection of voids in sensing lines used in the great number and variety of flow measurements necessary to the safe and viable operation of electric power generating plants employing nuclear reactors.

BACKGROUND OF THE INVENTION

1. Field of the Invention

The present invention relates to methods and means for detecting certain phase discontinuities in elongated liquid containment vessels or pipes, and more particularly to a new and novel technique and attendant apparatus for the effecting of same, which technique, and method thereof has been proven to be highly effective and accurate for detecting voids such as gas bubbles or, for that matter, complete gas blockages in liquid containment means.

It will be appreciated by those skilled in the art that the detection of gas bubbles or gas pockets within a liquid is of substantial importance in the effective and proper monitoring and controlling of a wide variety of processes. For example, transmission of pressure through liquid-filled sensing lines is affected by air within the lines. Air that completely fills the cross section of a sensing line can cause an error in transmission of static, or mean, pressure proportional to the vertical height of the air void. In addition, both small air bubbles and large air voids change the natural frequencies for pressure wave propagation in a sensing line (the standing wave frequencies) and, consequently, affect transmission of dynamic pressure fluctuations through the line. If the lowest natural frequency is reduced, by air, into the sensitive range of the pressure transmitter connected to a line, the transmitter signal can becomes significantly degraded by oscillations about the mean value of pressure.

As another example, in the operation of high temperature processes wherein are utilized liquid coolants the presence of gas bubbles within the coolant liquid can cause the heat transfer rate to be reduced wherever the bubbles are located, resulting in a lower overall heat transfer rate.

2. Description of the Prior Art

Numerous prior investigators have discovered, taught, and disclosed methods and means for detecting and monitoring the presence of discontinuities or inhomogeneities in fluids, such as for example gas bubbles in a liquid, and in particular in a liquid-filled pipe or other conduit.

The visual observation technique, employing an in situ sight glass or window, has been a rather popular innovation for detecting bubbles in liquid-filled pipes and one version has been familiar to a large section of the general population, at least up until the last several years, in the form of means for inspecting and determining the refrigerant sufficiency of many automotive air conditioners.

Liebermann, in U.S. Pat. No. 3,046,780, July 31, 1962, discloses a fluid condition monitor comprising a towable acoustic resonator and a pair of coupled transducers to detect impurities in the fluid through which it is towed by monitoring the quality factor, Q, of the resonating system. While it is suggested that this device can be used in pipelines, it would clearly be preferable to utilize a detection device which need not be placed within the mainstream of flow of fluid in the pipe or conduit.

Nakamoto, et al., in U.S. Pat. No. 4,144,741, Mar. 20, 1979, teach the concept of detecting voids or bubbles in a flowing liquid medium by inserting a detector in the flowing medium. The detector consists of one exciting coil attached to an AC signal applied thereto and two detecting coils located near the exciting coil. The outputs from the detecting coils provide means for detecting voids in the fluid.

The following three prior art references also show means for detecting voids or bubbles in a flow line and they also utilize transducers attached to the walls of the fluid-conveying pipe for inducing acoustical waves through the pipe and detecting the output through a second transducer (Blanchard, U.S. Pat. No. 2,573,390, Oct. 30, 1951; Wonn, U.S. Pat. No. 4,130,010, Dec. 19, 1978; and Liebermann, U.S. Pat. No. 4,235,095, Nov. 25, 1980).

The following three prior art references teach means for utilizing ultrasonic signals to detect bubbles in liquids; however, they have the distinct disadvantage of employing the use of rather complicated and expensive electronics in both the transmitting and receiving circuits (Taylor, U.S. Pat. No. 4,014,206, Mar. 29, 1977; McKnight, U.S. Pat. No. 4,112,735, Sept. 12, 1978; and Stasz, et al., U.S. Pat. No. 4,122,713, Oct. 31, 1978).

The concept of exciting standing waves in a fluid flowing medium is shown by Heisig, et al., U.S. Pat. No. 3,283,562, Nov. 8, 1962. The procedure includes coupling a transducer to the outer wall of a pipe and inducing signals through the pipe and the medium flowing therein to excite the standing waves of the medium. The resultant vibrations are detected by a second transducer which passes the signal through a demodulator whereby a trace is provided which will show or give an observation of a bubble passing through the pipe section in the region of the transducers. The input transducer is pulsed in a specific frequency band to avoid buildup of standing waves, a free air resonant frequency of the input transducer will then be known. The transducer is then excited to cause standing waves in the cavity whereby the output of the output transducer will indicate passage of the bubbles in the fluid.

There is no suggestion in any of the above prior art references of the technique of the present invention for using measured shifts in standing wave frequencies to detect the presence of gas voids in liquid-filled conduits. Nor is there any suggestion in the prior art references of the technique of introducing a pressure transient into a liquid-filled conduit in order to excite standing waves in the conduit. More particularly, there is no suggestion of methods or means suitable for detecting discontinuities, including voids, in conduits such as the sensing lines used in flow measurements necessary to the operation of nuclear power plants. In the teachings of the prior art references, the modus operandi is the detection of bubbles in the fluid as the bubbles are directed past a particular region or area physically near the detector. In operation of the technique of the instant invention, however, the bubbles in liquid do not need to be directed to or past a transducer; i.e., they may be physically located quite far from the detection device and the liquid need not be flowing.

SUMMARY OF THE INVENTION

The instant invention relates to a vastly improved technique, including methods and means, for detecting voids in liquid-filled conduits which technique uses measurements of the frequencies of standing waves present either because of background flow noise in the conduit (passive technique) or because of excitation by an induced pressure transient (active technique). The standing wave frequencies are determined from a Fourier transform of pressure fluctuations in the conduit which pressure fluctuations are measured using a pressure transducer, for example, a hydrophone.

The instant invention relies on measurements of the frequencies of the standing waves characteristic to liquid-filled conduit systems. These standing waves are elastic, or acoustic, waves that propagate through liquid in conduits at a propagation velocity, or celerity, that depends on the compressibility of the liquid and on the elasticity of the conduit walls. Characteristic to every conduit system is an infinite number of natural, resonant frequencies at which standing waves can oscillate within the fluid. The natural frequencies of these standing waves depend primarily on the wave celerity and on the geometry of the conduit system, including the number and arrangement of pipes, the presence of valves and other appurtenances, and the conditions at the system boundaries. Because gases are more compressible than liquids, the natural frequencies of the characteristic standing pressure waves in a conduit are shifted by air, or other gas, from their values with no air.

The instant invention relies on reference measurements of the standing wave frequencies taken after the piping system has been purged of air. Later measurements can then be compared with the reference values. Standing wave frequencies that are shifted relative to their values with no air indicate the presence of air.

The instant invention is applied as either an active or as a passive technique, where both techniques use measurements of standing wave frequencies and differ only in the manner in which the standing waves are excited. When the active technique is used, a conduit's standing wave frequencies are excited by abruptly reducing the pressure at some point along the conduit, thus inducing a pressure transient. The energy in a sharp transient is spread throughout a relatively broad range of the frequency spectrum. The liquid in a conduit will respond to broad-band pressure excitation with pressure oscillations primarily at the standing wave frequencies characteristic for the line. When the passive technique is used, a conduit's standing wave frequencies are excited by background flow noise. Turbulence in flow provides a source of random noise containing energy spread throughout a range of the frequency spectrum. A conduit conveying, or attached to another conduit conveying, a turbulent flow responds to this random energy input with pressure fluctuations primarily at the standing wave frequencies of the line. Consequently, if the noise signal is sufficiently strong, the standing wave frequencies of a conduit, can be determined from measurements of the background flow noise.

In both techniques, pressure fluctuations are measured with a pressure transducer, for example a hydrophone. Fourier transform techniques are used to decompose the pressure signal into its various frequency components. Standing wave frequencies are represented as peaks in the frequency spectrum.

OBJECTS OF THE INVENTION

It is a principal object of the present invention to provide a new method for easily, quickly, and accurately detecting the presence of bubbles or pockets of air or other gas in liquid-filled sensing lines used in power plants to transmit pressure from various process lines to pressure transmitters.

Another principal object of the present invention is to provide a method for air detection in sensing lines that can be used without interrupting transmission of the pressure signal from the process line and that does not provide an opportunity for water to spill or leak from the sensing line.

A still further object of the present invention is to provide a method for air detection that includes a signal processor that unambiguously indicates whether a significant quantity of air is, or is not, present in a sensing line without requiring the user of the invention to possess advanced knowledge of the principles on which the invention is based.

A more general object of the present invention is to provide a new method for detecting the presence of air or gas-filled voids in any liquid conduit system whether the contained liquid is flowing or nonflowing.

Still further and more general objects and advantages of the present invention will appear from the more detailed description set forth below, it being understood, however, that this more detailed description is given by way of illustration and explanation only, and not necessarily by way of limitation since various changes therein may be made by those skilled in the art without departing from the true spirit and scope of the present invention.

BRIEF DESCRIPTION OF THE DRAWINGS

The present invention will be better understood from a consideration of the following description taken in connection with the accompanying drawings in which:

FIG. 3 diagrammatically illustrates a simplified sensing line containing a quantity of air.

DETAILED DESCRIPTION OF THE DRAWINGS

For the sake of clarity and a better understanding of the applicability of the diagrams as well as the graphical illustrations presented in the various drawings, specifically FIGS. 2(A) through 10 supra, a more detailed description of same is given below in combination with the description of Examples I through III. A more detailed description of FIG. 1 is incorporated into the description of the preferred embodiment below.

DESCRIPTION OF A PREFERRED EMBODIMENT

The principal objective and purpose of the present invention is the development of a suitable air detector for liquid-filled sensing lines to effect the detection of the presence of air bubbles or voids in power plant sensing lines. In order for the desired technique described supra to be suitable for use in such power plants, the means and method of the air detector must meet the following criteria: (a) the technique either must be able to measure flow noise existing in the sensing line or must introduce a measurable transient pressure pulse; (b) it must not interrupt the transmission of process line mean pressure through the sensing line; (c) it should include a signal processor that unambiguously indicates whether a significant quantity of air is, or is not, present in the sensing line; and (d) it should (at least for some applications) not present an opportunity for water to spill, or leak, from a sensing line. The void detection system of the present invention was developed for the particular purpose of detecting the presence of air in sensing lines, which are small in diameter and are non-flowing. However, the instant technique, including methods and means therefore, also is capable of void detection in larger pipes and in pipes containing liquid flow.

Figure 1:
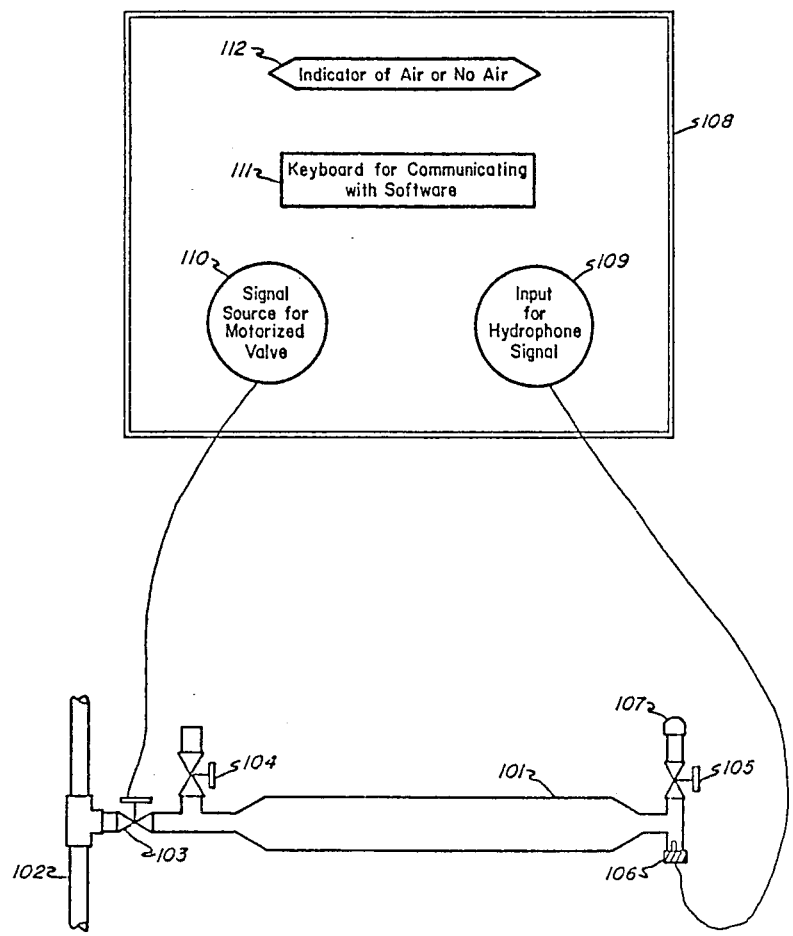
FIG. 1 illustrates by means of conceptual design, a prototype sensing line air detection system as used in a power plant, including the processing electronics referred to as the Void Detection Analyzer (VDA).

Referring now more specifically to FIG. 1, therein is shown a conceptual design for a prototype air detector in a power plant. The device shown can utilize either the active or the passive technique for air detection. As may be seen, the detector system consists of short pipe section 101 (normally a few feet long), of larger diameter than sensing line 102; valves 103, 104, and 105; hydrophone 106; and signal processing device, or "Void Detection Analyzer" 108 (VDA). Pipe section 101, with valves 103-105 and hydrophone 106, can be teed into sensing line 102 at any convenient location. Either a pipe section similar to pipe section 101 can be installed in each of several sensing lines similar to sensing line 102 or a portable attachment can be designed. Regardless, only one signal processing device, or VDA 108, would be required for a power plant. The attachment can be simplified for sensing lines for which the passive technique of listening to background flow noise can be exclusively applied. These lines require only that a hydrophone be connected in contact with the sensing line liquid and thereby transmit a signal representing the flow noise to VDA 108. The short section of pipe and various valves are required only for the active technique.

In order to function as an air detector, the attachment illustrated in FIG. 1 must first be free of air itself. Several alternatives for purging air from the attachment are provided for. Air may be flushed from the attachment by removing pipe cap 107, opening valves 103, 104, and 105, and running water from sensing line 102 through said open valves. Alternatively, hoses attached to the risers containing valves 104 and 105 can supply water to flush the attachment through valve 103 into sensing line 102 (back flushing). An additional alternative is to attach a water supply to the riser above either valve 104 or valve 105 and allowing the water to flow out of the other valve. Whichever alternative is used, it is important that the the attachment be as free of air as possible before operating the device.

The active technique is utilized by reducing the presence in attached pipe 101 to less than sensing line 102 pressure and subsequently opening valve 103, which may be a manually operated valve or a motorized valve, thus introducing a pressure transient into sensing line 102. Use of a motorized valve, rather than a manual valve, to initiate the transient permits the process to be controlled by electronics 110, if desired. There are two alternative methods for reducing the pressure in the attachment. Using the first method, the pressure is reduced to ambient (atmospheric) by briefly opening either valve 104 or valve 105 (with pipe cap 107 removed). Two disadvantages of this method are (1) that water would spill from sensing line 102 if valve 103 happened to be open when valve 104 or 105 was opened, and (2) the magnitude of the pressure reduction cannot be controlled (the pressure is always reduced to atmospheric). In the alternative method, valve 105, which may be a gate or a needle valve, is partially or fully closed when the water in attached pipe section 101 is under full sensing line 102 pressure and pipe cap 107 is in place. After valve 103 is closed, valve 105 is opened somewhat, causing the valve body (not shown) to partially move out of the water in the riser. This leaves a small space for water to flow into, which relieves strain in the pipe walls and thus decreases the water pressure. The amount that the pressure is decreased should depend on how far valve 105 is opened, so that the magnitude of the pressure reduction can be controlled. The water volume associated with the strained pipe walls is so small that an appropriate valve can reduce the pressure as far as atmospheric, if desired. This design has the additional advantage of providing no opportunity for water to spill.

The VDA of the present invention can take several different forms. Minimally it must be capable of accepting a hydrophone signal, processing the signal, and displaying the result. As a processor, the VDA should be capable of performing Fourier transforms on pressure signals and averaging several signals together to minimize the effects of noise. Also, the sampling frequency and filters in the VDA should be designed both to provide a variable frequency bandwidth and to avoid signal aliasing. Appropriate window functions should be available to avoid signal leakage. Most commercially available spectrum analyzers can fulfill the function of the minimal VDA if they are used by a person skilled in the art.

FIG. 1 depicts a preferred embodiment of such VDA 108, which can be operated by a person not necessarily skilled in the art. VDA 108 contains the signal processing capabilities discussed above along with a memory for storing reference measurements of standing wave frequencies for sensing lines containing no air. VDA 108 is microcomputer based and contains software capable of comparing a present measurement with a previous measurement stored in memory in order to determine from this comparison whether air is, or is not, present in the sensing line. In this preferred embodiment of VDA 108, the operator sees only what is depicted in FIG. 1: input port 109 to accept hydrophone 106 signal; signal source 110 to active valve 103, if it is motorized; keyboard 111 used to indicate to the software the identity of the sensing line being tested; and message on video display terminal 112, or alternatively a light, or some other indication (not shown) of the result of the test, which is, simply, whether air is, or is not, present. All of these requirements can be satisfied using a microcomputer system. If the temperature of the water in a sensing line varies significantly with time, it might be necessary to add a water temperature measurement to the instant void detection system. The standing wave frequencies for a piping system vary predictably with water temperature.

To minimize effects on the process line pressure measurement when the active technique is used, the pressure pulse introduced into sensing line 102 should only be large enough to ensure an adequately strong signal at hydrophone 106. Because the magnitude of the pressure pulse introduced by opening valve 103 is a function primarily of the pressure differential across said valve, it may be desirable to control this pressure differential using the alternative method discussed above for reducing the attachment pressure. In addition to its magnitude, the ability of a pressure transient to excite standing waves depends on the volume of water contained in pipe attachment 101 (its length and diameter).

The choice of whether to use the active or the passive technique for air detection in a given situation is not always obvious. Each technique has advantages and disadvantges.

Experience has shown that the passive technique is capable of reliably detecting the presence of relatively small quantities of air located anywhere within a sensing line containing sufficient flow noise. The primary disadvantage of this technique compared with the active technique is the time required to complete a test. Determination of the standing wave frequencies from measurements of flow noise requires that many measurements (40 during field tests) be averaged together to remove extraneous noise. The frequency range that is typically appropriate for relatively long (say 300 feet) plant sensing line is 0 to 100 Hz. For this frequency range, each measurement takes about 8 seconds. If 40 measurements are to be averaged, the total measurement time is about 5 minutes.

The signal received by the hydrophone when the active technique is used to induce a pressure transient is sufficiently "clean" that few (perhaps 5) measurements need to be averaged, and a test can take less than a minute. The active technique is capable of detecting air in sensing lines with or without flow noise, unless the air is located very close to the process line. Both laboratory and field tests suggest that the pressure transient induced using the active technique can excite only the several lowest-frequency standing wave modes. Consequently, for air to be detectable using the active technique, the air must affect the frequencies of these lowest modes. Calculations and tests indicate that even relatively small quantities of air affect these modes unless the air is positioned within a short distance, relative to the length of the sensing line, from the process line.

For subsequent comparison, both the active and passive techniques for void detection, i.e., air, require values of the standing wave frequencies of a sensing line when it contains no air or, at least, an insignificant quantity of air. Although it may sometimes prove difficult to completely purge a prototype sensing line of air, it is believed that a carefully purged line should not contain enough air to affect the process line pressure measurement. This amount of air is therefore insignificant and values of the standing wave frequencies obtained after careful purging should prove to be adequate as references.

EXAMPLES

In order that those skilled in the art may better understand how the present invention can be practiced, the following examples are given by way of illustration only.

EXAMPLE I

In the pursuit of further information gathered for the purposes of more clearly defining the parameters affecting the practice of the instant invention, the investigations herein, which are based on the proposition that the standing wave frequencies and mode shapes for any piping system and the effects of air on same can be computed, were made.

Figure 2A:
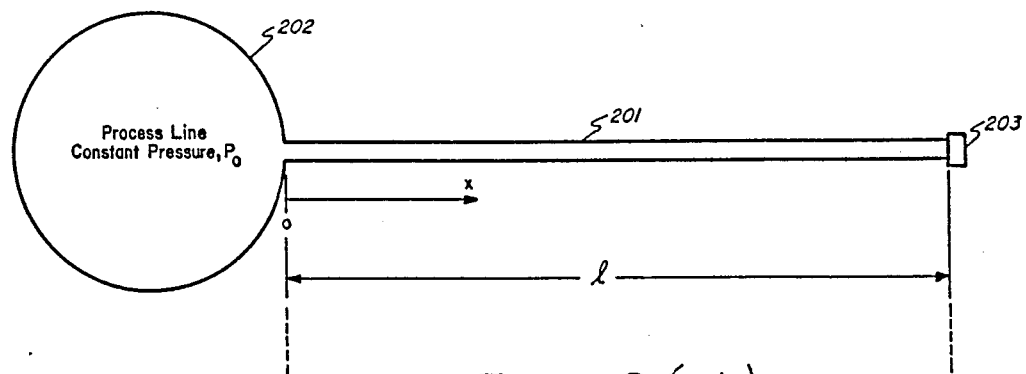
FIGS. 2(A) and 2(B) diagrammatically illustrate a simplified sensing line along with the mode shapes of its three lowest frequency standing waves.
Figure 2B:
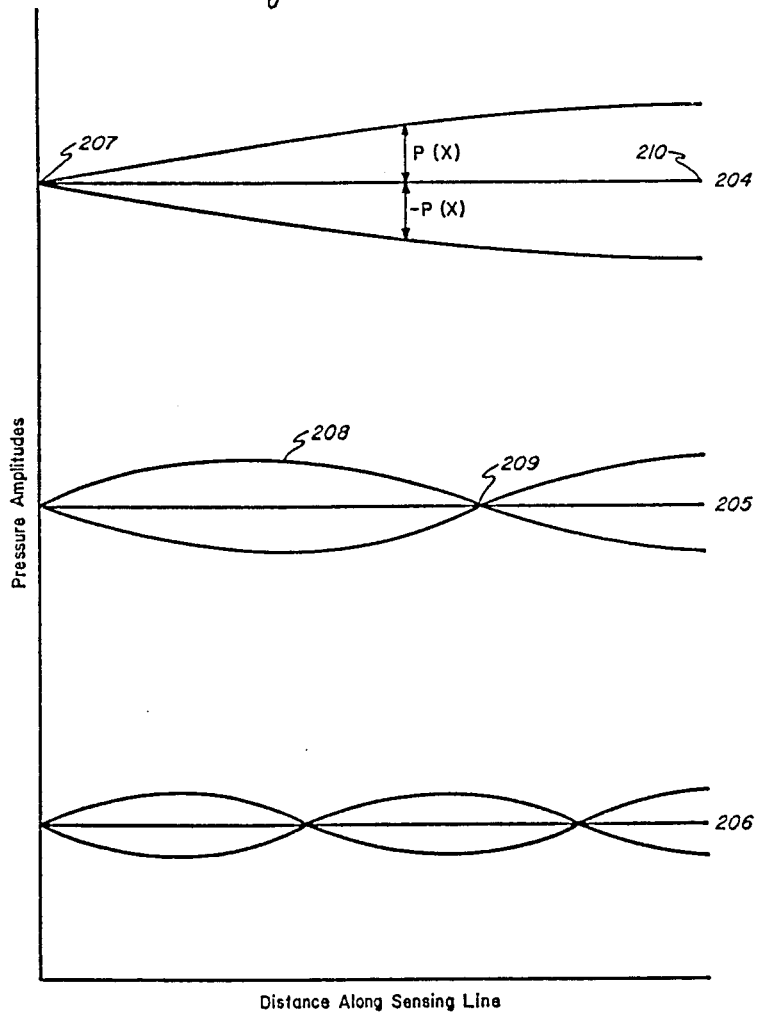

Referring now more specifically to FIGS. 2(A) and 2(B), therein is depicted in FIG. 2(B), for the herein general purpose of describing standing pressure waves and demonstrating the effect of air on their natural frequencies, as a projection of simple sensing line 201 in communication with process line 202 and pressure transmitter 203 in FIG. 2(A), the mode shapes of sensing line's 201 three lowest frequency standing waves, i.e., mode 1 shown as 204; mode 2 shown as 205; and mode 3 shown as 206. In this depiction of FIG. 2(B), the x-axis represents the distance along sensing line 201 and the y-axis generally represents pressure amplitudes of the three modes 204-206. Accordingly, the mode shapes show the amplitude, P, as a function of position, x, in FIG. 2A, of the pressure oscillations associated with each standing wave. The mode shapes are determined by the physics governing pressure wave propagation through the liquid in a pipe and by the boundary conditions at each end of the pipe.

As shown at 207 for mode 204, the boundary at which the sensing line intersects the process line is a pressure node—a point at which the pressure oscillations for every standing wave are zero. The process pressure is unaffected by the standing pressure waves in the sensing line because the diameter of the process line is much larger than the diameter of the sensing line.

For this example, the boundary represented by pressure transmitter 203 is assumed to be a dead-end, which is shown for mode 204 as flow node or pressure antinode 210. Neither a steady nor an oscillatory flow can exist at a flow node. Further examples of pressure antinodes and nodes are illustrated for mode 2, i.e., 205, at 208 and 209, respectively.

For this simple example, the standing waves are sinusoids of wavelength, $\lambda_k$, where k refers to the mode number. The natural frequency, f, of a sinusoidal standing wave is equal to the wave celerity, a, divided by the wavelength, $\lambda$. The celerity of standing pressure waves is the speed of sound in the water within the pipe. By inspection, the sinusoids that define the three mode shapes in FIG. 2(B) supra have wavelengths 4l, 4l/3, and 4l/5, respectively, where l in FIG. 2(A) is the length of sensing line 201. The simple sensing line has an infinite number of characteristic standing waves. In general, the wavelength of mode k is $4l/(2k-1)$. Thus, the natural frequency of the $k^{th}$ mode standing wave is $$f_k = \frac{(2k-1)a}{4l} \quad (1)$$

The natural frequencies increase with k, and each mode shape contains k pressure nodes (including the boundary node at the process line).

Analysis of the simple sensing line depicted in FIGS. 2(A) and 2(B) supra provides insight into the phenomenon of standing pressure waves in sensing lines. However, Equation (1) does not necessarily apply to real power plant sensing lines, which may be bounded by relatively compliant pressure transmitters and may have multiple bends and tees. The mode shapes of the standing waves in real sensing lines are not as simple as those depicted in FIG. 2(B) supra and, accordingly, the mathematical description of the standing wave frequencies is not as simple as that expressed by Equation (1).

The effects of air on the standing wave frequencies and mode shapes for a sensing line increase with increasing air volume and decreasing mean pressure. The effects of air are also influenced by its distribution within a sensing line. These effects will be illustrated infra.

Referring now more specifically to FIG. 3, therein is depicted simple sensing line 301 of length l and cross-sectional area A bounded on one end by pressure transmitter 302, assumed to be a dead end for flow, and on the other end by process line 303, assumed to be a point of constant pressure (a pressure node). Air pocket, generally shown as pipe riser 304, of volume $V_a$ under mean pressure $P_a$ is assumed to be located a distance $\xi$ from process line 303. The standing wave frequencies for sensing line 301 can be determined by applying methods described by Wylie and Streeter, *Fluid Transients*, (McGraw-Hill, 1978). Using these methods the following equation, which contains the standing wave frequencies (values of $\omega$) as roots, can be derived:

$$\cos(\pi\omega^*) - GF \sin(\pi\omega^*\xi) \cos[\pi\omega^*(1-\xi^*)] = 0 \quad (2)$$

In Equation (2), the following dimensionless quantities are defined:

$$\omega^* = \frac{\omega l}{\pi a}, \quad \xi^* = \frac{\xi}{l}, \quad G = \frac{V_a/A}{nP_a/\rho g}, \quad F = \frac{a^2}{gl} \quad (3)$$

in which a=acoustic wave speed (as discussed supra), n=polytropic exponent of the air, $\rho$=density of water in sensing line, and g=acceleration of gravity. Equation (2) expresses the dimensionless frequency, $\omega^*$, as a function only of the product G*F (GF), which accounts for the effects of added air, and the dimensionless position of the added air, $\xi^*$. Calculations using Equation (2) indicate that the present invention should be able to detect the presence of a quantity of air so long as the volume of the air and the pressure on the air are of such values that the product GF is greater than about 0.05.

Figure 4:
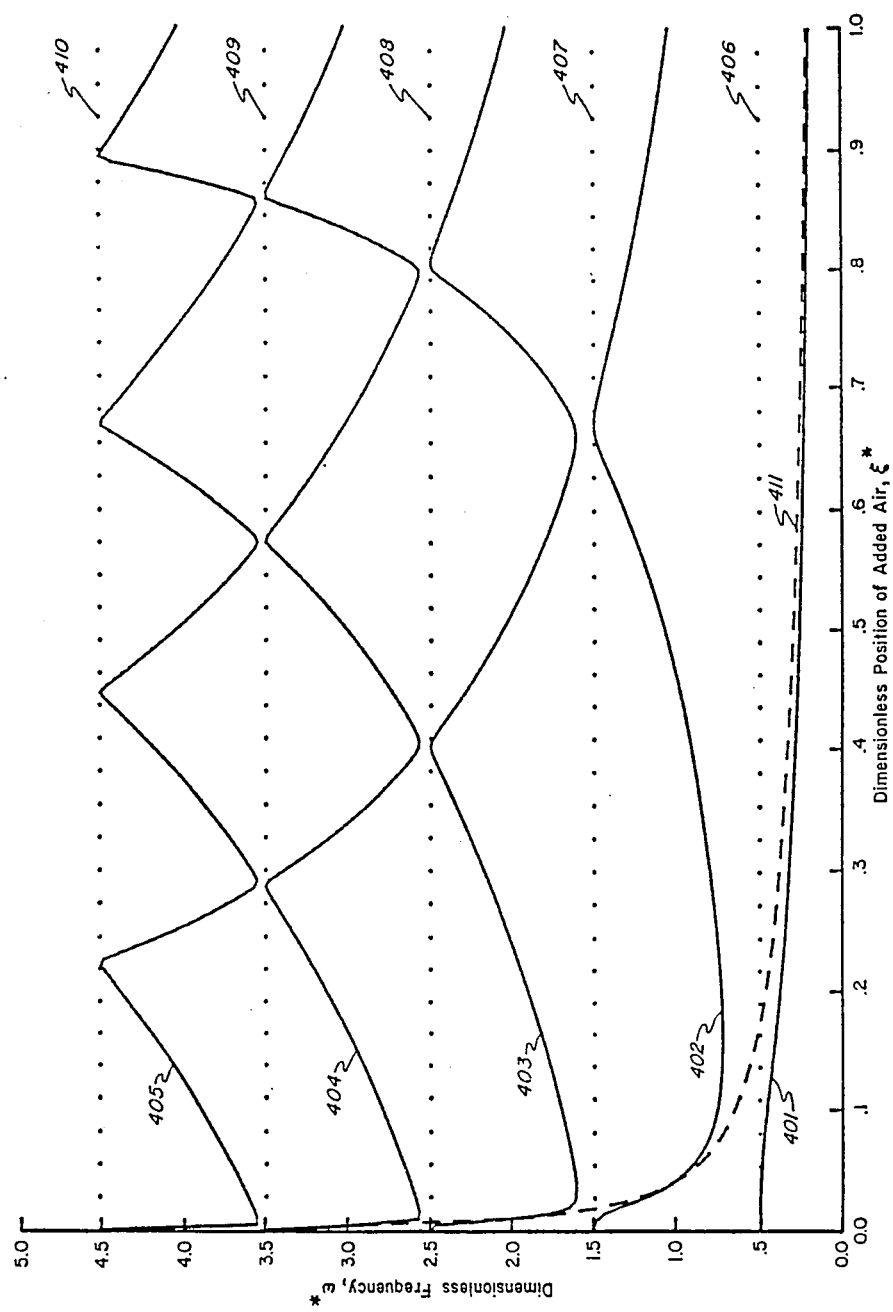
FIGS. 4 and 5 graphically illustrate the effects of an air pocket's location along a sensing line on the standing wave frequencies for the line.

Referring now more specifically to FIG. 4, therein is illustrated the effects on standing wave frequencies of location of an air pocket along a simple sensing line. For this example, GF is assumed to equal 2.35, which corresponds approximately to a 4-inch long air column under 100 psia pressure in a ½-inch diameter sensing line that is 300 feet long. The dimensionless frequencies of the first five standing wave modes, with air, as determined by finding the roots of Equation (2) supra, i.e., modes 1–5 are represented by solid-line curves, 401–405. Dotted horizontal lines, 406–410 represent the standing wave frequencies without air in the line of modes 1–5, respectively. Dashed curve, 411, corresponds to surge oscillation frequencies due to the air, which are discussed infra. The points in FIG. 4 where the solid curves intersect the dotted lines are pressure nodes, which are points at which air may be positioned without affecting the natural frequency of a standing wave mode. Note that the frequencies of all five standing wave modes are reduced by air located anywhere along the sensing line, except at pressure nodes.

The conclusion to be drawn from FIG. 4 supra is that air added anywhere along a sensing line, except very near the process line, significantly affects at least four of the five lowest-frequency standing wave modes. In fact, the relatively small amount of air assumed for this example should be detectable even if only the first two modes are measured unless the air location corresponds to $\xi^*$ less than about 0.01. When air is located very near the process line, higher frequency modes are affected more than are lower frequency modes.

Figure 5:
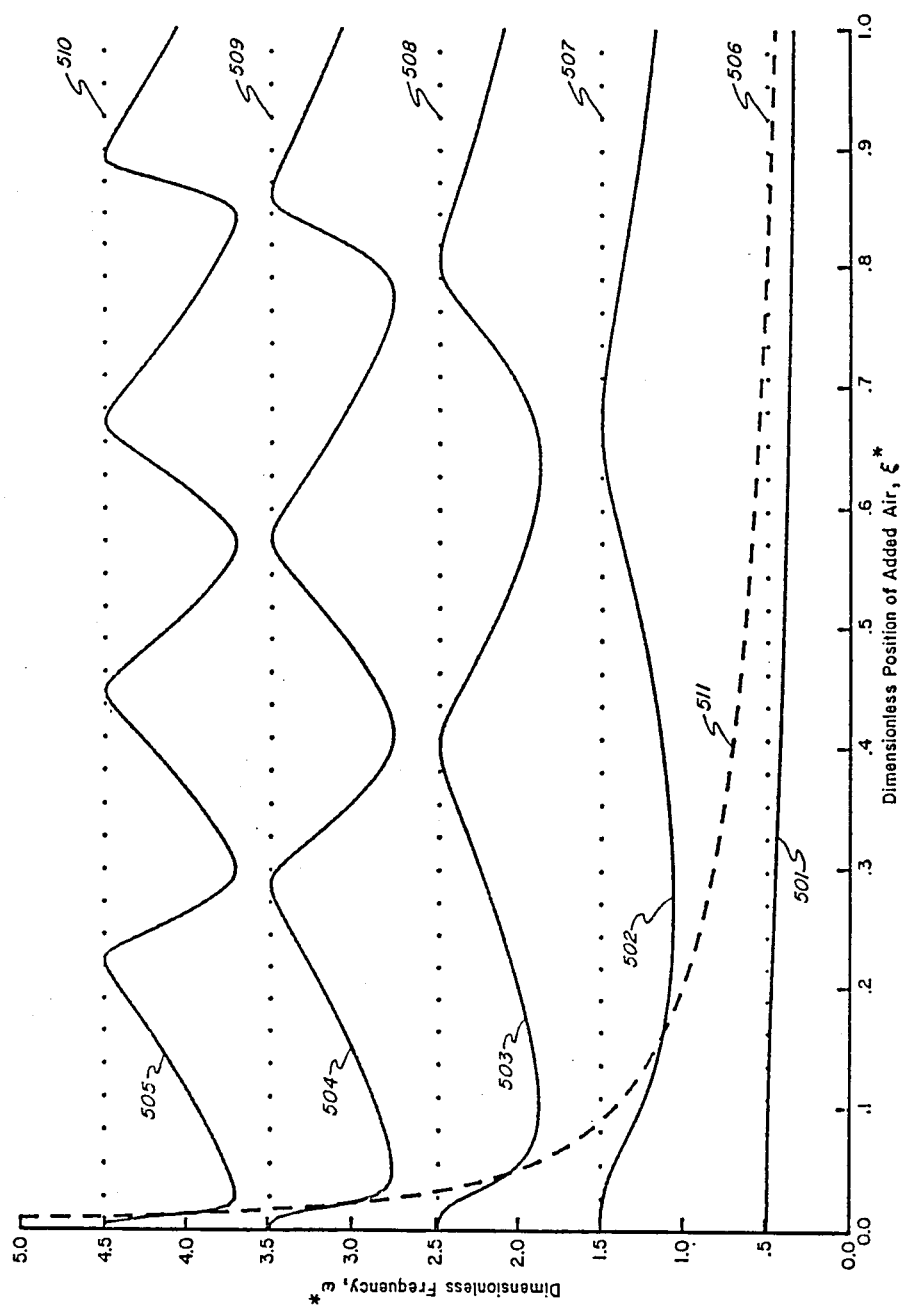

In a fashion similiar to the layout of FIG. 4 supra, and referring now more specifically to FIG. 5 the dimensionless frequencies of the first five standing wave modes, with air, as determined by finding the roots of Equation (2) supra, i.e., modes 1–5 are represented by solid-line curves, 501–505. Dotted horizontal lines, 506–510 represent the standing wave frequencies without air in the line of modes 1–5, respectively. Dashed curve, 511, corresponds to surge oscillation frequencies due to the air, which are discussed infra. Referring now more specifically to FIG. 5, therein is illustrated the effect of air location for GF=0.5, i.e., about 1/5th of the volume of air assumed for the calculations displayed in FIG. 4 supra. This volume of air under 100 psia pressure represents an air column less than 1-inch long in a ½-inch diameter sensing line that is 300 feet long. The conclusions drawn from FIG. 4 also apply to FIG. 5, with one modification: an amount of air corresponding to GF=0.5 would be difficult to detect by a technique that only excited the first two standing wave modes if the air is located closer to the process line than about $\xi^*=0.05$.

FIGS. 4 and 5 supra illustrate that the nearer air is to the process line and the smaller the quantity of air, the higher in the frequency spectrum it is necessary to look in order to detect it.

Air in a sensing line provides internal spring-like boundaries for surge oscillations, which refer to harmonic oscillations of water columns acting as rigid masses. A single pocket of air in a sensing line acts as a spring to the water column between the process line and the air. The surge oscillation associated with an air pocket is of interest because the effects of air on the frequencies of standing waves are most significant for standing wave modes whose frequencies are greater than or nearly equal to the surge oscillation frequency. Standing wave modes with natural frequencies significantly less than the surge oscillation frequency are only slightly affected by the air.

A reasonable estimate of the natural frequency of the surge oscillation mode associated with air can be obtained by treating the spring-mass system composed of the water column and air pocket as a simple harmonic oscillator with stiffness, K, due to the air and mass, M, of the water column. In terms of the dimensionless variables defined supra, the surge oscillation frequency, $\omega_s^*$, can be expressed as $$\omega_s^* = \frac{1}{\pi} \sqrt{\frac{1}{\xi^* GF}} \tag{4}$$

Small air pockets under high pressure are relatively "stiff" (small GF) and result in relatively high-frequency surge oscillations. Large air pockets under low pressure are relatively "soft" (large GF) and result in low-frequency surge oscillations.

Dashed curves 411 and 511 in FIGS. 4 and 5, respectively, represent Equation (4) with GF equal to 2.35 and 0.5, respectively. Notice that for GF=2.35, the first mode's natural frequency is nearly equal to the surge frequency for $\xi^*$ greater than about 0.2. In general, for relatively soft air pockets, the frequency of the first mode tends to be near the surge frequency unless the air is very close to the process line.

In FIG. 4 supra, notice also that for $\xi^*$ less than about 0.1, the frequencies of the standing wave modes above dashed curve 411 are reduced by the air nearly to the no-air frequencies of the modes below them. This effect leads to the appearance that the addition of air causes a new natural frequency to occur with the frequencies of all standing wave modes above the new frequency increasing. Examination of the mode shapes indicates that, for air very close to the process line, this interpretation is reasonable. The new frequency is nearly equal to the surge frequency due to the air, as predicted by Equation (4). The mode shapes of standing waves with frequencies above the surge oscillation mode are nearly identical to the mode shapes, computed without air in the line, of the standing waves that precede them in mode number.

In contrast to the simplicity of the sensing lines depicted in FIGS. 2(A) and 3 supra, power plant sensing lines often contain multiple bends, tees, valves, and riser pipes. Because these elements reflect wave energy, they influence the standing wave frequencies and mode shapes for a sensing line. However, air influences the more complicated standing wave modes of a real sensing line just as it does the simple modes of a simplified sensing line. Furthermore, the methods described by Wylie and Streeter, *Fluid Transients*, (McGraw-Hill, 1978), can be applied to compute the natural frequencies and mode shapes of sensing lines of any complexity. However, for the sake of practicality computer calculations are necessary for sensing lines that are much more complicated than the sensing lines portrayed in FIGS. 2(A) and 3.

EXAMPLE II

Figure 6:
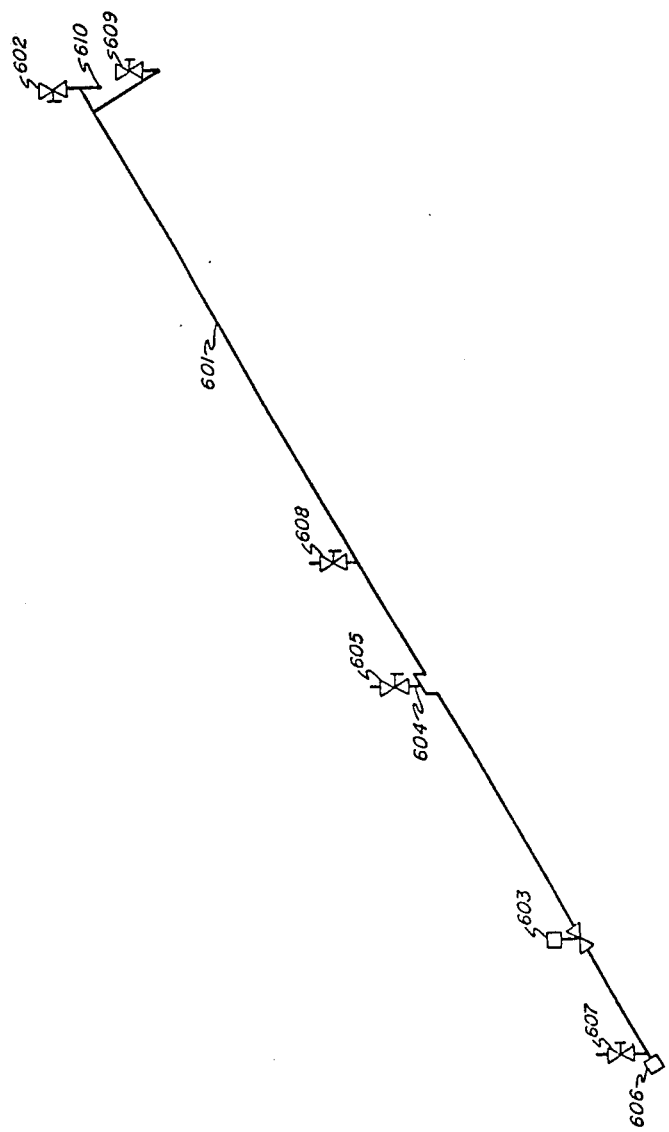
FIG. 6 illustrates by means of schematic diagram an experimental sensing line, including location of valves, water supply, and a hydrophone used to measure pressure fluctuations.

Referring now more specifically to FIG. 6, therein is illustrated a laboratory piping system used to provide a further example that air can be detected in piping using measurements of standing wave frequencies. Said piping system comprised about 87 feet of ½-inch SCH 40 galvanized water pipe, 601. Pipe 601 was pressurized to about 75 psia using the water supply above valve 602. Valve 603, a solenoid valve, could be opened or closed in less than 0.15 seconds. When desired, air was introduced into riser 604 under valve 605. Fluctuations in water pressure within pipe 601 were measured using hydrophone 606, inserted in pipe 601 at the end thereof opposite to the water supply above valve 602 supra. A dynamic signal analyzer (not shown) processed the signals from hydrophone 606.

With several bends, tees, valves and riser pipes, pipe 601 as illustrated, is more representative of a power plant sensing line than is the simplified sensing line depicted in FIGS. 2(A) and 2(B) supra. However, in contrast to a power plant sensing line which would have a pressure node at its point of intersection with the process line, the boundaries of the experimental pipe 601 were all flow nodes. The experiments were conducted with valve 602 and all the other boundary valves closed. Consequently, the standing wave mode shapes for experimental pipe 601 are different from those that would be characteristic of a power plant sensing line. However, the principle that air reduces standing wave frequencies in piping systems is independent of boundary conditions and associated differences in mode shapes.

The active technique was tested in pipe 601. Standing waves were excited by inducing a sharp pressure transient. With solenoid valve 603 closed, that portion of pipe 601 on the water-supply side of solenoid valve 603 was pressurized to approximately 75 psia by briefly opening valve 602. The pressure in pipe 601 in that section between hydrophone 606 and solenoid valve 603 was then reduced to atmospheric by briefly opening valve 607. This procedure established a pressure discontinuity across solenoid valve 603. The pressure transient was initiated by suddenly opening solenoid valve 603, which caused a positive pressure wave to propagate towards hydrophone 606. In order to facilitate a better understanding of the specifics of the layout shown in FIG. 6, Table I is included infra. Where dimensions are shown from pipe 601, i.e., 601 as a reference point, it is to be understood that same relate to distances that a particular apparatus is positioned normal to pipe 601, whereas all other dimensions are measured along the length of pipe 601.

TABLE I

| Reference Point | Object | Distance (in feet) |
|---|---|---|
| 606 | 607 | 0.2 |
| 606 | 603 | 10.8 |
| 603 | 604 | 21.0 |
| 604 | 608 | 11.1 |
| 608 | 609 | 39.8 |
| 609 | 602 | 0.8 |
| 601 | 604 | 0.7 |
| 601 | 609 | 3.2 |
| 601 | 610 | 0.9 |

Figure 7:
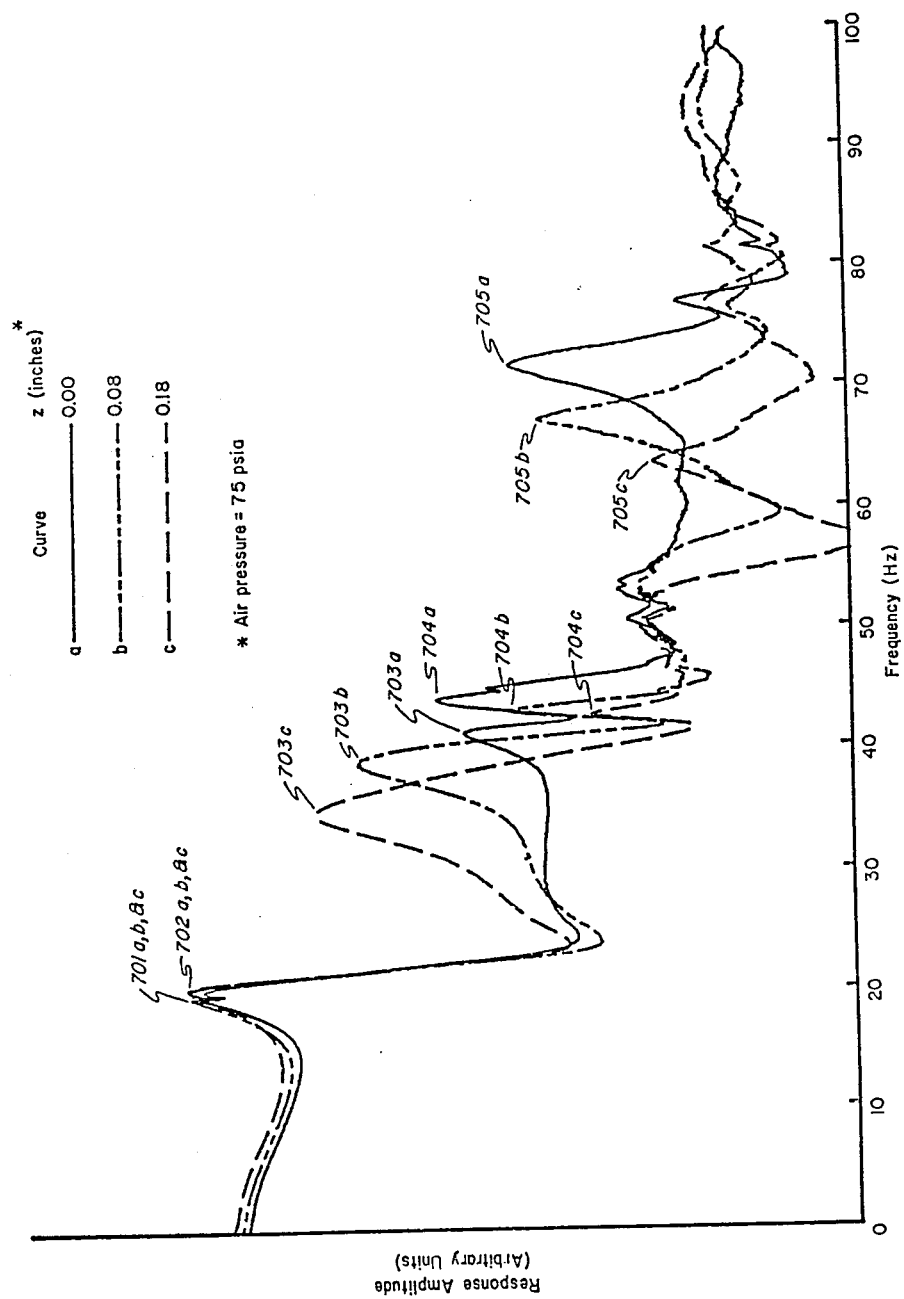
FIG. 7 graphically illustrates the reduction in the standing wave frequencies of the experimental piping system illustrated in FIG. 6 supra due to increasing amounts of added air. These spectra were obtained using the active technique for air detection.

Referring now more specifically to FIG. 7, therein are presented typical power spectra of the pressure response at hydrophone 606 following the introduction of a pressure transient into pipe 601 with and without small amounts of air introduced under valve 605, all from FIG. 6, supra. The power spectra indicate the distribution of the pressure fluctuations over the frequency range 0 to 100 Hz. Several maxima in each spectrum are evident in FIG. 7. The maxima representing standing wave frequencies (mode Nos.) are shown for convenience, it being understood that the maxima for modes number 1 and 2 are so close that they are simply herein grouped together. Without computer calculations, the mode shapes that correspond to each standing wave frequency are not obvious. However, it is reasonably clear that the two low-frequency maxima near 20 Hz correspond to first mode standing waves stretched between points 606 and 609 and points 606 and 602, respectively, in FIG. 6, supra. The maxima labeled 703, 704, and 705 are various harmonics of the first two maxima, i.e., 701 and 702 each for a, b, and c.

In FIG. 7, the quantity of air is denoted by the length, z, of an air column with cross-sectional area equal to the internal cross-sectional area of the sensing line. Note that $z=0.08$ inches corresponds to the product $GF=0.21$ and $z=0.18$ inches corresponds to $GF=0.48$. The frequencies of modes 3, 4, and 5 were reduced by the air. However, the frequencies of modes 1 and 2 were unaffected by the air because the air location was very near a pressure node for each of these modes. For these two modes, which represent standing waves between boundaries that are pressure antinodes, the interior pressure node would normally be expected to be near the center of the piping. However, solenoid valve 603 (FIG. 6) contained a spring and diaphragm that is more compressible than the water. This "soft spot" caused the interior node to be shifted to the air location. That the frequency of mode 4 was only slightly reduced by the air suggests that this mode also had a pressure node near valve 605 (of FIG. 6).

EXAMPLE III

Figure 8:
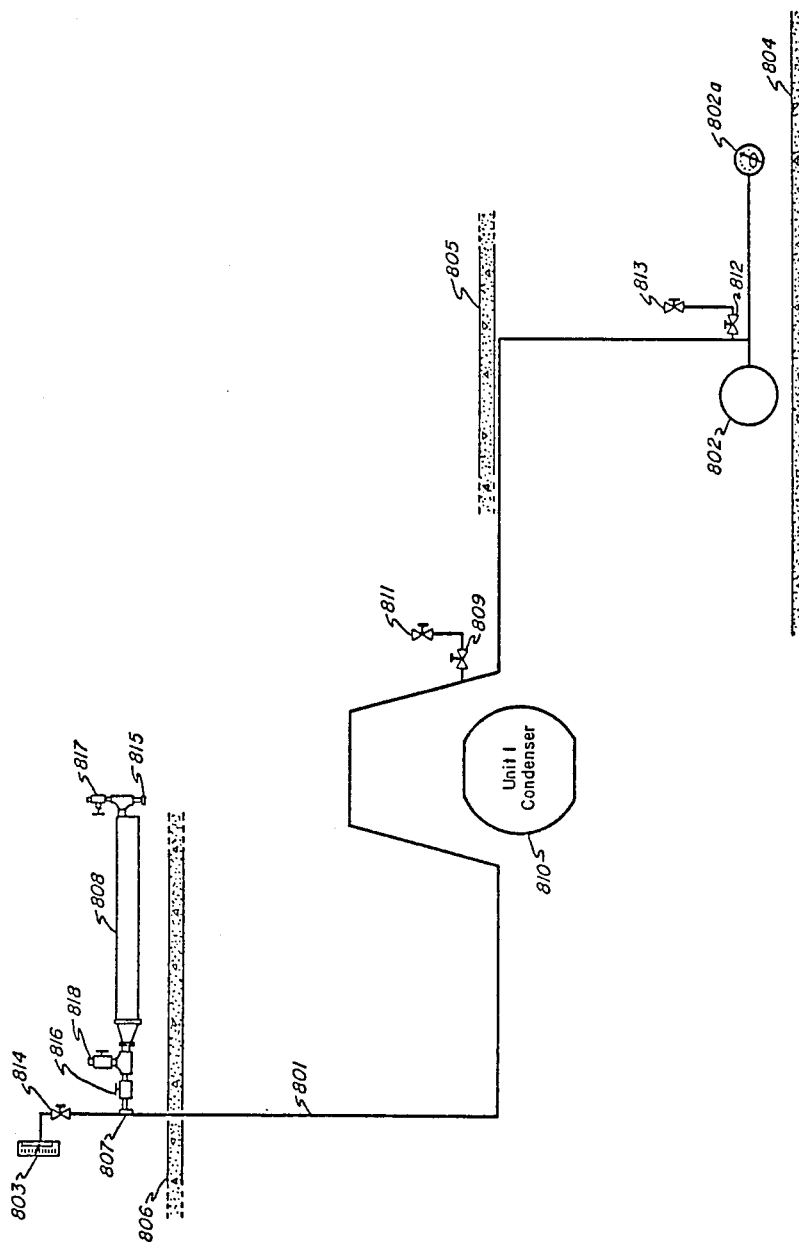
FIG. 8 illustrates by means of schematic diagram a sensing line at the Tennessee Valley Authority's Kingston Steam Plant which was used for tests of the present invention.

Referring now more specifically to FIG. 8, therein is approximately depicted sensing line 801 leading from the discharge of the Unit 1 raw water service pump 802 at Kingston Steam Plant to pressure gauge 803 in the control room for Units 1 and 2. Line 801 was used to provide a further example that air can be detected in sensing lines using measurements of standing wave frequencies. Both the passive and active techniques were tested. Line 801 which was constructed of ⅜-inch copper had a total length of approximately 264 feet (based on a measurement accurate to about plus or minus 5 feet) including an elevation gain of about 45 feet between pump 802, located in the powerhouse basement, and control room pressure gauge 803. Note that pump 802 was operatively connected to attendant pressure gauge 802a. The basement floor (EL.725) is generally shown at 804; the mezzanine floor (EL.744) is generally shown at 805; and the operating level floor (EL.765) is generally shown at 806. At least 10 bends (not all illustrated), most of which are 90-degree elbows, are included in line 801.

As illustrated, four modifications to the sensing line were made for the tests: (1) tee 807 was installed in sensing line 801 under control room pressure gauge 803 to provide a location at which void detection apparatus 808 could be attached; (2) tee 809 was installed in line 801 near Unit 1 condenser 810 to provide a location for air insertion means, generally illustrated as 811; (3) tee 812 was installed in line 801 near pump 802 for air insertion means, generally illustrated as 813; and (4) valve 814 was installed in line 801 just below control room pressure gauge 803 to isolate gauge 803 during some of the tests. Under atmospheric pressure, the maximum volume of the air pockets that could be established in the L-shaped, ½-inch pipes, 811 or 813, attached for air insertion was about 0.0025 cubic feet (70 ml). Taking pressure into account, the maximum volumes of the air pockets that could be established were about 0.00029 cubic feet near pump 802 (127 psia), and 0.00031 cubic feet near condenser 810 (118 psia). In terms of length of an air column in sensing line 801, these volumes of air translate to approximately 4 inches. Note that, in terms of the parameters defined in Example I supra, the locations for air insertion correspond to $\xi^*=0.0068$ for location 813 near pump 802 and $\xi^*=0.35$ for location 811 near condenser 810. The product GF is approximately 2.0 for both locations.

For the particular results reported herein, in-line isolation valve 814 below control room pressure gauge 803 was closed. Then, measurements taken after attempting to purge line 801 of air were compared with measurements taken after air was inserted. Although tests were conducted with air inserted both near pump 802 and near condenser 810, for the sake of brevity, only results from tests in which air was inserted near condenser 810 are reported herein. Calculations and previous results indicated that line 801 was not entirely purged of air during these tests; that is, some air remained despite all efforts to remove it. Nevertheless, as demonstrated infra, the additional air added near condenser 810 was easily detected.

For tests of the passive technique, the background flow noise was measured using hydrophone 815 in void detector 808. To remove the random content of the signals, leaving the periodic content, spectra obtained from 40 consecutive time records, each 8 seconds long, were averaged together. Consequently, each final spectrum required about 5.3 minutes of data.

For tests of the active technique, standing waves were excited in sensing line 801 by inducing a sharp pressure transient at void detector 808. As illustrated, in-line valve 816 (a ½-inch ball valve) separated void detector 808 from sensing line 801. With valve 816 closed, the pressure in water-filled void detector 808 was reduced to atmospheric by briefly opening valve 817 above hydrophone 815. This procedure established a pressure discontinuity across closed, in-line valve 816. The pressure transient was then initiated by suddenly opening in-line valve 816. Five measurements were averaged together to obtain the final spectrum.

Figure 9:
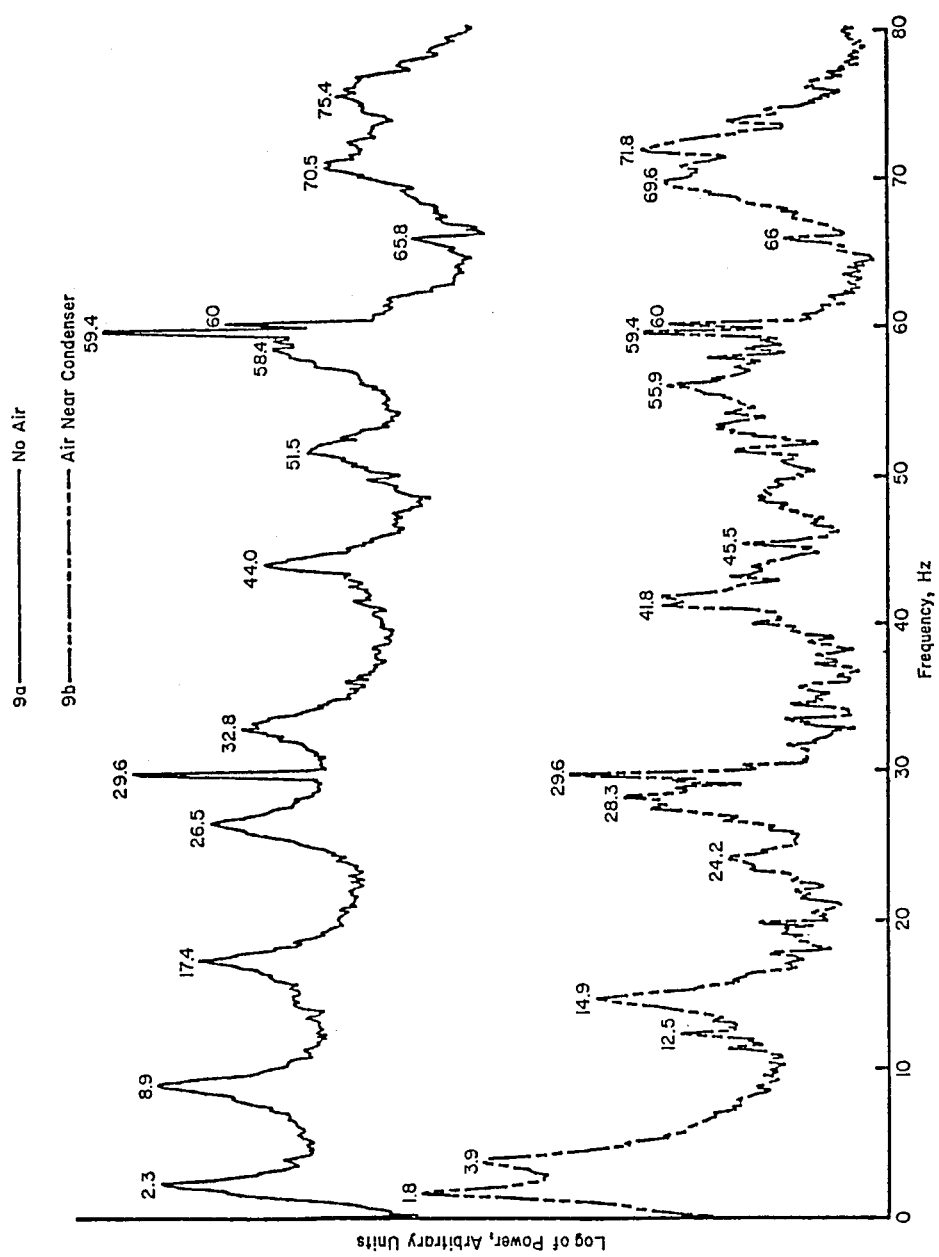
FIG. 9 graphically illustrates by means of frequency spectra the effects on standing wave frequencies, measured using the passive technique for air detection, of air added to the sensing line illustrated in FIG. 8 supra.

Referring now more specifically to FIG. 9, therein is presented power spectra of the background flow noise in the raw water sensing line. Graph 9a shows the spectrum measured when line 801, of FIG. 8 supra, contained no added air (No Air) and Graph 9b shows the measurement after air was added at 813, of FIG. 8 supra, i.e., near condenser 810 (Air Near Condenser). The added air reduced the lowest standing wave frequency from 2.3 to 1.8 Hz, and generally shifted all the standing wave frequencies labeled in Graph 9a. In Graph 9b, the peak at 1.8 Hz approximately corresponds to surge oscillation of the water column between the process line and the added air, with the air pocket acting as a spring. The peaks at 29.6 and 59.4 Hz correspond to the pump's (802 in FIG. 8) rotational frequency and its first harmonic, respectively. The peaks at 60 Hz are due to electrical noise.

Figure 10:
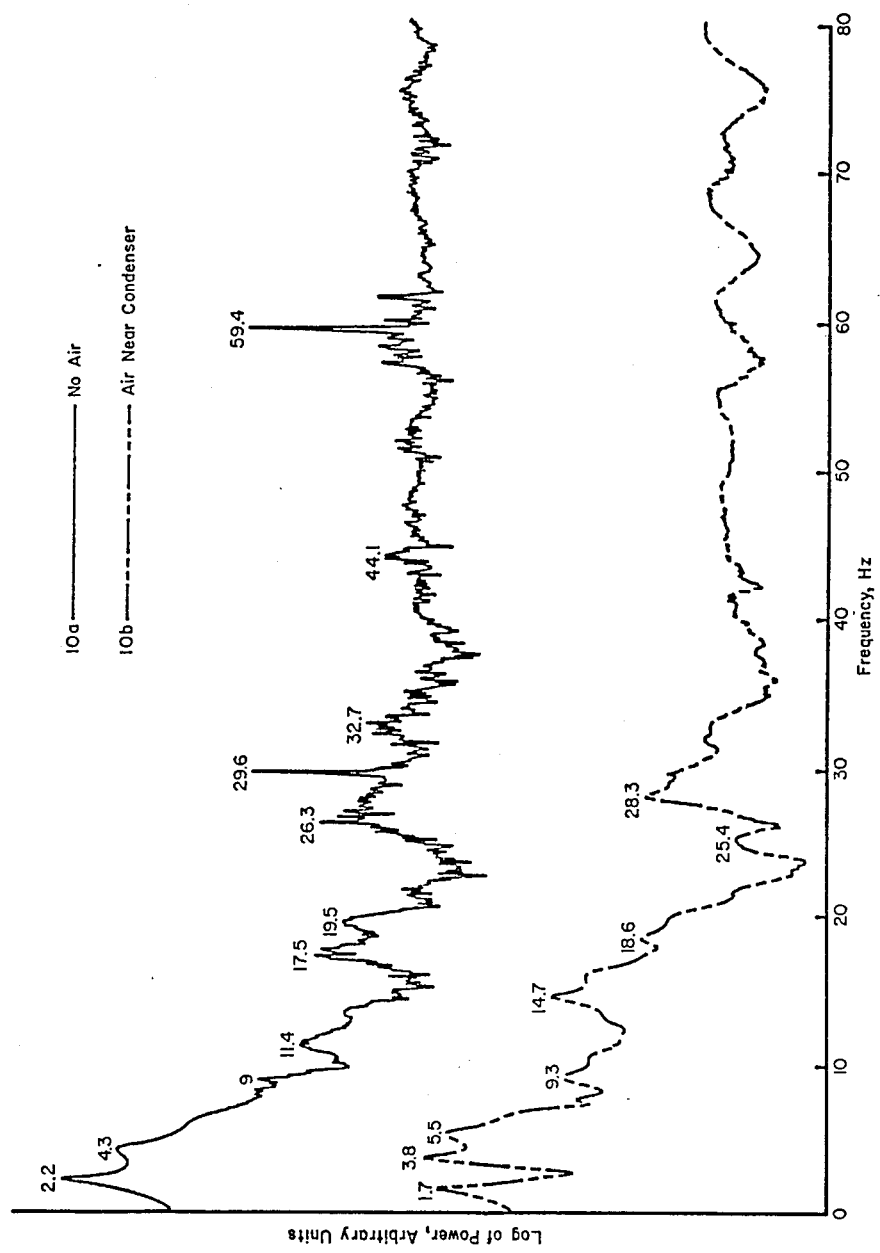
FIG. 10 graphically illustrates by means of frequency spectra the effects on standing wave frequencies, measured using the active technique for air detection, of air added to the sensing line illustrated in FIG. 8 supra.

Referring now more specifically to FIG. 10, therein is presented a comparison of a spectrum obtained using the active technique with no added air with a spectrum obtained with air added near the condenser, at 813 in FIG. 8 supra. In these spectra, the energy in the induced transients is concentrated below about 15 Hz in Graph 10a and below about 30 Hz in Graph 10b. Above 15 Hz in Graph 10a, the background flow noise is evident. Consequently, only a few of the lowest standing wave modes were excited by the active technique, particularly before air was added near the condenser. Nevertheless, as evident, the added air caused significant changes in the standing wave frequencies.

INVENTION PARAMETERS

The data presented supra, as well as other results and operations of our new, novel, and improved technique, including methods and means for the effecting thereof, indicate the ranges of various operating variables, and acceptable and preferred conditions for carrying out our invention. These indications are summarized below.

The following considerations apply to implementations of both the active and passive techniques:

1. The product GF, defined in Example I supra, determines the minimum quantity of gas detectable by the present invention. Quantities of gas leading to values of GF greater than about 0.05 should be detectable in general, and even smaller quantities may be detectable under favorable conditions.

2. A minimum of two standing wave frequencies must be measured for reliable gas detection in conduit means. Measurement of five to ten standing wave frequencies is preferable. There is little point in measuring more than 10 frequencies. The minimum of two is acceptable only if two are all that are available, which is sometimes the case when the active technique is used.

3. The frequency range over which to measure is chosen to contain the desired number of standing wave frequencies. The magnitude of the standing wave frequencies, and thus of the frequency range, depends on the geometry of the conduit means. This range is determined best by trial when reference measurements are obtained without gas in the conduit means. The determined frequency range can than be used in later measurements. Alternatively, Equation (1) supra can be used to estimate the standing wave frequencies for a conduit means and thus estimate the required frequency range.

4. The transducer employed to measure the pressure fluctuations is preferably a hydrophone, or similar transducer, which measures only the fluctuating part of a pressure signal and does not sense the mean pressure. The measuring range of transducers that sense mean pressure often precludes accurate measurement of pressure fluctuations about the mean. Yet it is the fluctuations, not the mean, from which the standing wave frequencies are derived.

5. Regardless of its size or geometry, the attachment illustrated in FIG. 1 supra affects, at least slightly, the values of the standing wave frequencies measured for the conduit means. Consequently, for accurate determination of the presence of gas in the conduit means, it is important that the same attachment be used for both the no gas reference measurements and for the subsequent detection measurements.

The passive technique is preferable to the active technique in conduits containing sufficient noise and for which the test time is not critical. It is simpler and capable of measuring a larger number of standing waves than is the active technique. For the passive technique, the attachment, illustrated in FIG. 1 supra, must hold the hydrophone used to sense pressure fluctuations and the temperature sensing instrument, if required. The dimensions and size of the attachment are irrelevant (except that the same attachment used to measure the no gas reference signal must be used for the subsequent detection tests as well).

The active technique is preferable to the passive technique in conduits containing insufficient noise for the passive technique, and in situations in which the time to perform a test is of prime importance. Ranges for various operating variables of the active technique are discussed below:

1. The time to perform a gas detection test using the active technique is typically 5 to 20 times less than the time to perform a gas detection test using the passive technique.

2. For application of the active technique, the dimensions of the attached pipe section, illustrated in FIG. 1 supra, are chosen such that the volume of liquid contained within said attached pipe section is between 2 and 10 percent of the total volume of liquid within the conduit means to which the void detection apparatus is attached. Thus, the dimensions of said attachment are specified in order to hold a certain volume of liquid rather than to be a certain length or certain cross-sectional area. Typically, a convenient length (a few feet if possible) is chosen for said attached pipe section and then its cross section properties are chosen to produce an acceptable volume.

3. The valve used to induce a pressure transient (valve 103 in FIG. 1, supra) should not present a spring-like boundary to the liquid within the attached pipe section. A rigid valve, such as a ball or gate valve, operated manually or motorized is best. Some solenoid valves are not acceptable for general use. A valve containing a diaphragm and spring, like for instance the solenoid valve used for the laboratory tests in Example II supra, may cause a nonlinear pressure response and can significantly affect the standing wave frequencies of the system comprising the conduit means and the attachment. (For the specific conditions under which the laboratory tests were performed, the solenoid valve was satisfactory.)

4. The valve used to induce a pressure transient must be opened rapidly to generate an adequate transient, generally within a second or two.

5. The magnitude of the pressure transient induced by the active technique depends on the magnitude of the pressure differential set up between the conduit means and the attachment before the transient-inducing valve within the attachment is opened. In most cases, this pressure differential should be between about 50 and 150 psi. If the pressure differential is less than 50 psi, in some cases the energy in the induced transient may be insufficient to produce adequate pressure fluctuations. If the pressure differential is greater than 150 psi, an undesirable nonlinear pressure response may be generated. However, to avoid damaging the conduit means, the strength of the conduit means must always be considered before specifying the pressure differential.

While we have shown and described particular embodiments of our invention, modifications and variations thereof will occur to those skilled in the art. We wish it to be understood therefore that the appended claims are intended to cover such modifications and variations which are within the true spirit and scope of our invention.

What we claim as new and desire to secure by Letters Patent of the United States is:

1. A passive comparative standing wave frequency system eminently suitable for measuring and comparing the characteristics of a fluid static in or flowing through containment means, said containment means including first conduit means, and said measuring of characteristics including detecting inhomogeneities comprising air pockets, gas bubbles or both in said fluid within said first conduit means, said system comprising:
   (a) void detection attachment means, said void detection attachment means comprising:
      (1) second conduit means for containing a relatively small portion of fluid, said second conduit means operatively associated with said first conduit means;
      (2) pressure response detecting means operatively associated with said second conduit means; and
   (b) pressure response analyzer means coupled to receive the output from said pressure response detecting means, said pressure response analyzer means comprising:
      (1) power spectrum indicative means for providing, over a predetermined frequency range, the distribution of the pressure fluctuations sensed by said pressure response detecting means, said pressure fluctuations effected in situ in said first conduit means by virtue of the background flow noise therein;
      (2) storage means for the resulting distribution of said pressure fluctuations;
      (3) retrieval means operatively associated with said storage means and with later mentioned standing wave frequency comparator means; and
      (4) standing wave frequency comparator means for effecting a comparison between the frequency distribution of said pressure fluctuations with previously stored frequency distributions, said previously stored frequency distributions subsequently retrieved from said storage means by said retrieval means, and said standing wave frequency comparator means thereby operable to detect a change in the quantitative value of inhomogeneities in said fluid within said first conduit means.

2. The comparative standing wave frequency system of claim 1, wherein said portion of fluid contained in said second conduit means ranges from about 2 to about 10 percent, on a volume basis, of the fluid contained in said first conduit means.

3. The comparative standing wave frequency system of claim 2, wherein said pressure response detecting means comprises a hydrophone.

4. The comparative standing wave frequency system of claim 3, wherein fluid temperature detecting means is operatively associated with said void detection attachment means and coupled with said pressure response analyzer means to receive the output from said fluid temperature detecting means.

5. The comparative standing wave frequency system of claim 4, wherein said power spectrum indicative means provides, over frequencies ranging upwards to about 100 Hz, said distribution of said pressure fluctuations.

6. The comparative standing wave frequency system of claim 4, wherein said power spectrum indicative means provides said distribution of said pressure fluctuations for about the first 2 to 10 standing wave frequencies characteristic of said first conduit means.

7. The comparative standing wave frequency system of claim 6, wherein the fluid in said containment means is subjected to pressures of such value and said inhomogeneities are gas bubbles or air pockets of such total volume that the product GF (G*F), is greater than about 0.05, and wherein $$G = \frac{V_a/A}{nP_a/\rho g}$$

where
$V_a$ = volume of inhomogeneity;
A = cross-sectional area of first conduit means;
n = polytropic exponent of inhomogeneity phase;
$P_a$ = mean pressure of inhomogeneity;
$\rho$ = density of fluid in first conduit means;
g = acceleration of gravity; and $$F = \frac{a^2}{gl}$$

where
a = acoustic wave speed;
g = gas supra; and
l = length of first conduit means.

8. The comparative standing wave frequency system of claim 7, wherein said power spectrum indicative means provides said distribution of said pressure fluctuations for about the first 2 to 5 standing wave frequencies characteristic of said first conduit means.

9. The comparative standing wave frequency system of claim 8, wherein said power spectrum indicative means provides said distribution of said pressure fluctuations for about the first 2 standing wave frequencies characteristic of said first conduit means.

10. A passive comparative standing wave frequency method eminently suitable for measuring and comparing the standing wave frequency characteristics of a fluid static in or flowing through containment means, said containment means including first conduit means, and said measuring of characteristics including detecting inhomogeneities comprising air pockets, gas bubbles, or both in said fluid within said first conduit means, said method comprising:
   (a) attaching void detection means to said first conduit means, said void detection means comprising second conduit means and pressure response detecting means, said second conduit means and said pressure response detecting means operatively associated one with the other;
   (b) introducing a portion of fluid into said second conduit means in quantity sufficient to substantially displace any voids therein, said second conduit means operatively associated with said void detection means, and said portion of fluid introduced into said second conduit means ranging from about 2 to about 10 percent, on a volume basis, of the fluid contained in said first conduit means;
   (c) establishing physical communion between said first and said second conduit means to effect coupling of the pressure fluctuations characteristic in said first conduit means, by virtue of the background flow noise therein, with said pressure response detecting means in said second conduit means;

(d) coupling the output from said pressure response detecting means with pressure response analyzer means, said pressure response analyzer means comprising power spectrum indicative means, storage means, retrieval means, and standing wave frequency comparator means, said power spectrum indicative means and said retrieval means operatively associated with said standing wave frequency comparator means;

(e) deriving from said power spectrum indicative means, over a predetermined frequency range, the distribution of the pressure fluctuations sensed by said pressure response detecting means;

(f) retrieving from said storage means previously stored frequency distributions; and (g) comparing, by means of said standing wave frequency comparator means, said resulting retrieved and previously stored frequency distributions with said distribution of pressure fluctuations derived in step (e) supra, to thereby effect detection of a change in the quantitative value of inhomogeneities in said fluid within said first conduit means generally within the time period elapsed between the storage of said frequency distributions, or just prior thereto, and the derivation performed in step (e) supra.

11. The method of claim 10 wherein said power spectrum indicative means provides said distribution of said pressure fluctuations over the frequency range 0 to 100 Hz.

12. The method of claim 11 wherein said power spectrum indicative means provides said distribution of said pressure fluctuations for about the first 2 to 10 standing wave frequencies characteristic of said first conduit means.

13. The method of claim 12 wherein said power spectrum indicative means provides said distribution of said pressure fluctuations for about the first 2 to 5 standing wave frequencies characteristic of said first conduit means.

14. The method of claim 13 wherein said power spectrum indicative means provides said distribution of said pressure fluctuations for about the first 2 standing wave frequencies characteristic of said first conduit means.

* * * * *